(12) United States Patent
Aberl et al.

(10) Patent No.: US 7,723,124 B2
(45) Date of Patent: May 25, 2010

(54) METHOD FOR THE RAPID DIAGNOSIS OF TARGETS IN HUMAN BODY FLUIDS

(75) Inventors: Franz Aberl, Princeton, NJ (US); Marcus Scheibenzuber, Munich (DE); Robert F. Sambursky, Philadelphia, PA (US); Robert W. Vandine, Montoursville, PA (US); Jose S. Sambursky, Johnson City, NY (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 0 days.

(21) Appl. No.: 11/052,748

(22) Filed: Feb. 9, 2005

(65) Prior Publication Data

US 2005/0175992 A1   Aug. 11, 2005

Related U.S. Application Data

(60) Provisional application No. 60/542,303, filed on Feb. 9, 2004.

(51) Int. Cl.
*C12Q 1/68* (2006.01)
*G01N 21/00* (2006.01)
*G01N 15/06* (2006.01)
*G01N 21/77* (2006.01)
*G01N 1/18* (2006.01)
*G01N 33/53* (2006.01)
*B01L 3/00* (2006.01)

(52) U.S. Cl. .......................... 436/518; 422/50; 422/55; 422/56; 422/58; 422/61; 422/68.1; 422/99; 436/164; 436/169; 436/177; 436/178; 436/811

(58) Field of Classification Search .................... 422/55, 422/56, 58, 50, 61, 68.1, 99; 436/164, 169, 436/177, 178, 811, 518
See application file for complete search history.

(56) References Cited

U.S. PATENT DOCUMENTS

| 4,299,916 | A | * | 11/1981 | Litman et al. ................. 435/6 |
| 4,737,456 | A | | 4/1988 | Weng |
| 4,844,866 | A | | 7/1989 | Wallace et al. |
| 4,904,448 | A | * | 2/1990 | Kawahara .................... 422/56 |
| 4,968,633 | A | * | 11/1990 | Marcucci ..................... 436/513 |

(Continued)

FOREIGN PATENT DOCUMENTS

DE        19622503 C2      7/1998

(Continued)

OTHER PUBLICATIONS

Uchio, Eiichi; Aoki, Koki; Saitoh, Waka; Itoh, Norihiko and Shigeaki Ohno. "Rapid Diagnosis of Adenoviral Conjunctivitis on Conjunctival Swabs by 10-Minute Immunochromatography," Opthalmology. 104 (1997) 1294-1299.*

(Continued)

*Primary Examiner*—Gailene R Gabel
*Assistant Examiner*—Jacqueline Diramio
(74) *Attorney, Agent, or Firm*—Brown & Michaels, PC

(57) ABSTRACT

More particularly, the present invention relates to a method for the detection of a target, e.g. pathogen in a human body fluid wherein a body fluid sample is collected with a swab member.

13 Claims, 4 Drawing Sheets

U.S. PATENT DOCUMENTS

| | | | |
|---|---|---|---|
| 5,075,078 | A | 12/1991 | Osikowicz et al. |
| 5,120,643 | A | 6/1992 | Ching et al. |
| 5,451,504 | A | 9/1995 | Fitzpatrick et al. |
| 5,591,645 | A | 1/1997 | Rosenstein |
| 5,714,341 | A | 2/1998 | Thieme et al. |
| 5,714,389 | A | 2/1998 | Charlton et al. |
| 5,798,273 | A | 8/1998 | Shuler et al. |
| 5,989,921 | A | 11/1999 | Charlton et al. |
| 6,046,058 | A | 4/2000 | Sun |
| 6,087,184 | A | 7/2000 | Magginetti et al. |
| 6,187,598 | B1 | 2/2001 | May et al. |
| 6,221,678 | B1 | 4/2001 | Chandler |
| 6,375,896 | B1 | 4/2002 | Wuske et al. |
| 6,485,982 | B1 | 11/2002 | Charlton |
| 6,498,010 | B1 | 12/2002 | Fitzgerald et al. |
| 6,514,773 | B1 | 2/2003 | Klein et al. |
| 6,548,309 | B1* | 4/2003 | Moore et al. ............... 436/500 |
| 6,555,390 | B2* | 4/2003 | Chandler .................... 436/518 |
| RE38,430 | E | 2/2004 | Rosenstein |
| 6,716,641 | B1 | 4/2004 | Sundrehagen |
| 6,737,278 | B1 | 5/2004 | Carlsson et al. |
| 6,890,484 | B2* | 5/2005 | Bautista et al. ............... 422/58 |
| 7,109,042 | B2 | 9/2006 | May et al. |
| 7,300,750 | B2 | 11/2007 | Smart et al. |
| 7,393,697 | B2 | 7/2008 | Charlton |
| 2002/0036170 | A1 | 3/2002 | Harvey et al. |
| 2003/0049658 | A1 | 3/2003 | Smart et al. |
| 2003/0119083 | A1 | 6/2003 | Owens et al. |
| 2003/0232451 | A1 | 12/2003 | Casterlin et al. |
| 2004/0082077 | A1 | 4/2004 | Hu |
| 2004/0115831 | A1 | 6/2004 | Meathrel et al. |
| 2004/0161857 | A1 | 8/2004 | Yugawa et al. |
| 2004/0235189 | A1* | 11/2004 | Lu ............................. 436/514 |
| 2005/0142622 | A1 | 6/2005 | Sanders et al. |
| 2005/0148097 | A1 | 7/2005 | Mizukami |
| 2005/0181517 | A1* | 8/2005 | Chandler et al. ............ 436/169 |
| 2005/0244986 | A1 | 11/2005 | May et al. |
| 2006/0003390 | A1 | 1/2006 | Schaffler et al. |
| 2006/0024767 | A1 | 2/2006 | Hajizadeh et al. |
| 2006/0121626 | A1 | 6/2006 | Imrich |
| 2006/0172434 | A1 | 8/2006 | Rowell |

FOREIGN PATENT DOCUMENTS

| | | | |
|---|---|---|---|
| EP | 0699906 | * | 7/1995 |
| WO | 9415215 A1 | | 7/1994 |
| WO | 9936776 A1 | | 7/1999 |
| WO | 9960402 A1 | | 11/1999 |
| WO | WO 01/36975 A | | 5/2001 |

OTHER PUBLICATIONS

Toraason, Mark; Sussman, Gordon; Biagini, Raymond; Meade, Jean; Beezhold, Donald; and Dori Germolec. "Latex Allergy in the Workplace," Toxicological Sciences. 58 (2000) 5-14.*

Wambura et al., "Diagnosis of rinderpest in Tanzania by a Rapid Chromatographic Strip-Test", Tropical Animal Health and Production, vol. 32, No. 3, Jun. 2000, pp. 141-145.

Database Biosis, 'Online!, Biosciences Information Service, Aug. 1997, Uchio Eiichi et al, "Rapid diagnosis of adenoviral conjunctivitis on conjunctival swabs by 10-minute immunochromatography", vol. 104, No. 8, Aug. 1997, pp. 1294-1299, Abs. Only.

Sobanski et al., "Detection of Adenovirus and Rotavirus Antigens by an Immuno-Gold Lateral Flow Test and Ultrasound-Enhanced Latex Agglutination Assay", Journal of Medical Microbiology, vol. 50, No. 2, Feb. 2001, pp. 203.

Bruning et al. "A Rapid Chromatographic Strip Test for The Pen-side Diagnosis of Rinderpest Virus". Journal of Virological Methods 81, 143-154 (1999).

Sambursky, 501-K Summary of Safety and Effectiveness (Sep. 14, 2005). Sambursky et al., "A prospective blinded multi-center clinical trial to evaluate the efficacy of the recently FDA approved RPS Adeno Detector for detecting adenoviral conjunctivitis".

RPS/ Rapid Pathogen Screening—About RPS. http://web.archive.org/web/20051226105022/rps-tests.com/about.html. Dec. 26, 2005.

Kent. "Point-of-Care Screening for Conjunctivitis" Review of Opthalmology, vol. No. 12:4, Apr. 15, 2005, http://www.revophth.com/index.as?page=1-707.htm.

Sambursky et al. "The RPS Adeno Detector for Diagnosing Adenoviral Conjunctivitis", Opthalmology. 113:10, 2006 pp. 1758-1764.

Udeh et al. "Cost Effectiveness of a Point-of-Care Test for Adenoviral Conjunctivitis" The American Journal of the Medical Sciences, 336:3, 2008, pp. 254-264.

Sambursky, "Physicians Guide to RPS Adeno Detector™", http://www.eyecaresource.com/conditions/pink-eye/physician-guide.html, [Jun. 3, 2009].

American Medical Association Clears Path for Adenoviral Conjunctivitis 'Pink Eye' Detector, Nov. 8, 2007 Medical News Today, http://www.medicalnewstoday.com/articles/88067.php.

"Rapid test for pink eye may curb overuse of antibiotics", Jan. 26, 2009. http://www.stjohnshealthplans.net/news/pinkeyetest.aspx.

* cited by examiner

Fig. 1

1: absorbant pad
2: sample application zone
3: detection zone
4: waste pad
5: carrier backing

METHOD FOR THE RAPID DIAGNOSIS OF TARGETS IN HUMAN BODY FLUIDS

CROSS REFERENCE TO RELATED APPLICATION

This application claims the benefit of U.S. Provisional Application No. 60/542,303, filed Feb. 9, 2004.

TECHNICAL FIELD OF THE INVENTION

The present invention relates to a method for the detection of targets, e.g. pathogens and/or allergy-associated components in a human body fluid wherein a body fluid sample is collected with a swab member. The samples are transferred from the swab member to a sample analysis device, on which an analysis of the targets, e.g. by immunochemical or enzymatic means can take place. The test result may be displayed within a short period of time and can be directly read out by the user. Further, a test kit for carrying out the method of the invention is provided.

BACKGROUND OF THE INVENTION

Rapid, point-of-care analysis is becoming increasingly important in the diagnosis and treatment of various viral and other pathogenic microbiological agents (bacteria, others). Especially in the acute status of a infectious disease medical doctors have a need for immediate detection of the causal agent for the symptoms observed.

Prior art discloses a rapid assay for HIV specific antibodies in saliva samples. A saliva sample is gained by means of a sampling stick. The saliva sample is diluted in a sample buffer and a lateral flow immunoassay is dipped into the diluted saliva sample [U.S. Pat. No. 5,714,341].

German Patent Nr. DE19622503 suggests to apply lateral flow immunoassays for the detection of illegal narcotics in saliva or sweat.

Conjunctivitis, commonly known as red eye or pink eye, may be caused by several different agents including viruses, bacteria and allergens. Different etiologies require different treatments. Infectious conjunctivitis is typically contagious. Conjunctivitis is generally diagnosed clinically, by gross examination, and (during a routine eye exam) slit lamp biomicroscopy. This method does not provide information on the specific infectious agent. If specific (pathogen typing) diagnosis is necessary, swabs of the inferior fornix are sent for laboratory analysis to determine the type of pathogen. The preferred methods for laboratory analysis are cell culture with confirmatory direct immunofluorescence, ELISA or PCR. The disadvantage of this diagnostic strategy is that laboratory analysis needs typically between two and ten days, utilizes complex diagnostic equipment, and may require technical skill in both performing and interpreting results. This time period is problematic for a proper treatment of potentially infectious forms of conjunctivitis that cannot be specifically classified/connected with a certain pathogenic agent.

A publication by Uchio et al. (Opthalmology 104 (1997), 1294-1299) discloses a method for the detection of adenovirus in eye fluid specimens. The method comprises collecting a sample of eye fluid and detecting the analyte on a paper disc by enzyme immunoadsorption. The detection, however, lacks specificity and sensitivity.

Thus, it is the objective of the invention to provide a sensitive and rapid non-invasive method for the detection of pathogens, e.g. bacterial or viral infectious agents in body fluids.

SUMMARY OF THE INVENTION

In a first aspect, the present invention relates to a method for the detection of a target which is selected from pathogens and/or allergy-associated components in a body fluid comprising the steps:
(a) non-invasively collecting a body fluid sample with a swab member,
(b) transferring the sample to a application zone on a sample analysis device and
(c) analysing the sample.

In a further aspect, the invention relates to a method for diagnosing conjunctivitis comprising the steps:
(a) non-invasively collecting an eye fluid sample with a swab member,
(b) transferring the sample to a application zone on a sample analysis device and
(c) analysing the sample.

In still a further aspect, the invention relates to a test kit comprising
(a) a swab member for non-invasively collecting a body fluid sample,
(b) a sample analysis device comprising a detection zone, wherein the detection zone contains reagents for determining the presence and/or amount of at least one target which is selected from pathogens and/or allergy-associated components.

In still a further aspect, the invention relates to a test kit comprising
(a) a swab member for non-invasively collecting an eye fluid sample,
(b) a sample analysis device comprising a detection zone, wherein the detection zone contains reagents for determining the presence and/or amount of at least one target which is selected from pathogens and/or allergy-associated components wherein the target is a causative agent or mediator of conjunctivitis or a plurality of such causative agents and/or mediators.

DESCRIPTION OF THE DRAWINGS

FIG. 2 shows a plastic housing (6) containing the strip as shown in FIG. 1. A sample application window (7) is provided for bringing a swab member into contact with the strip. The test result is displayed in the read out window (8).

DETAILED DESCRIPTION OF PREFERRED EMBODIMENTS

The invention provides a sensitive and rapid method for the detection of targets, e.g. pathogens and/or allergy-associated components in samples collected by non-invasive means from a body fluid. The pathogens are selected from viruses, microorganisms, e.g. bacteria and parasites, e.g. amoebae or nematodes. The allergy-associated components are selected from allergens and anti-allergic components. The detection may comprise a direct detection of the target, e.g. the pathogen and/or the detection of antibodies against the target, e.g. the pathogen which are present in the fluid sample to be tested. Preferably, the method comprises a parallel determination of a plurality of targets.

The body fluid is preferably a fluid from a body surface selected from mucose membrane fluids (of the oral, nasal, vaginal, and ocular cavities) tears, secretions from glands and secretions from lesions or blisters, e.g. lesions or blisters on the skin. More preferably, the sample is selected from oral, nasal, ocular, genital and rectal fluids and secretions from skin lesions or blisters. Most preferably, the sample is an eye fluid. A significant advantage of the method is that results are provided within the medical consultation period, e.g. in few minutes. Preferably, the results are provided in a time period up to 20 minutes, more preferably up to 15 minutes. Also, as the test is noninvasive, it poses very little risk to the patient. Thus the best available treatment can be applied on a timely basis for a specific pathogen. A further advantage over prior art methods is that only a few microliters of sample are required to perform an analysis. The sample is preferably about 0.1 µl to about 100 µl, more preferably about 0.2 µl to about 20 µl and most preferably about 0.5 µl to about 10 µl.

The invention may be performed by means of a simple test kit. Handling of the test kit does not necessitate additional laboratory equipment, further handling of reagents or instrumentation. Another important advantage of the invention described below is that the detection limit is typically 10 to 100 times lower than currently available diagnostic tests because samples do not require dilution before they are transferred to the analysis device. Therefore the disclosed method has proven to be more sensitive and accurate than methods of the prior art.

The invention discloses a non-invasive method for the rapid and point-of-care determination of pathogens from body fluids. The method is suitable for diagnosis in human beings and animals, e.g. pets or livestock animals. A preferred application is the detection of pathogens in eye fluid, e.g. human eye fluid. In this embodiment the pathogen to be detected is a causative agent of conjunctivitis or a plurality of such causative agents. For example, the pathogen is selected from the group of adenoviruses, herpesviruses, chlamydiae, cytomegaloviruses and combinations thereof. More preferably, a plurality of pathogens are detected on a single sample analysis device. For example, the sample analysis device may allow a simultaneous detection of a plurality of pathogens, particularly of at least two, of at least three, of at least four or of at least five pathogens selected from the group consisting of adenoviruses, herpesviruses, chlamydiae, cytomegaloviruses, *pseudomonas, streptococci, haemophilus, staphylococci*, amoebae, particularly *Acanthamoeba* and nematodes, particularly *Onchocera volvulus*. More preferably, the method comprises a simultaneous detection of adenoviruses, herpesviruses, chlamydiae, cytomegaloviruses and *Acanthamoeba*.

In addition the invention provides a non-invasive method for the rapid and point-of-care determination of at least one allergy-associated component, particularly an allergen (e.g. pollen, dust, etc.) and/or an antiallergen, particularly a component which is produced in the body in response to an allergenic challenge (e.g. IgE, histamine, etc.), in a body fluid as described above. More particularly, the invention relates to methods and devices for the diagnosis of allergy-associated components in eye fluid, e.g. human eye fluid. In a preferred embodiment, the determination of at least one allergy-associated component may be combined with the determination of at least one pathogen as described above.

In the method of the invention, a body fluid sample is non-invasively collected with a collection device or swab member, respectively. The collection step preferably comprises wiping or dabbing the swab member over a surface of the body containing body fluid to be tested. Usually, the swab member is sterile. The swab member may be dry or pretreated with a fluid before the collection step. For example, using a gentle swirling motion, a sterile swab member may be applied to the body surface or mucous membrane of concern and allowed to capture any pathogens and/or allergy-associated components contained in the body fluid.

The swab member may be a part which is separate from the sample analysis device and the sample is transferred by contacting the sample analysis device with the swab member under conditions wherein at least a part of the sample on the swab member is transferred to the sample analysis device. In this embodiment, the swab member is preferably contacted with a sample application zone on the analysis device from which the sample is then transferred to the detection zone. The contact preferably comprises fixing the swab member in a contact position with the sample analysis device in which the sample collection zone of the swab member is in direct contact with the sample application zone of the analysis device. Thus, the swab member and/or the analysis device preferably comprises fixing means for providing a fixed contact between both parts in a predetermined position. Alternatively, the swab member may be an integrated part of the sample analysis device and the transfer comprises passing at least a part of the sample on the swab member to the detection zone on the sample analysis device.

The transfer of the sample from the swab member to the detection zone on the sample analysis device is preferably a direct transfer, i.e. the transfer takes place without pretreatment of the sample on the swab member. Preferably, the transfer comprises an elution of the sample from the swab member with an elution medium, e.g. a buffer or water. The elution medium may be added from an external source or may be provided e.g. as a reservoir within the analysis device. Further, the transfer is preferably a chromatographic and/or capillary transfer of fluid to the detection zone on the sample analysis device.

In a preferred embodiment, the sample analysis device comprises a chromatographic test strip, e.g. a lateral flow test strip. The sample analysis device may comprise a sample application zone, a detection zone, optionally a waste zone, optionally a carrier backing, optionally a housing and optionally an opening for result read out. The sample analysis in the detection zone may be carried out by standard means, e.g. by an immunological or enzymatic detection method. Preferably, the detection method comprises the use of test reagents capable of specifically binding the targets, e.g. pathogens to be tested or antibodies or other receptors against these targets, e.g. pathogens and subsequent visualisation of the bound entity, e.g. by enzymatic detection or by means of direct labelling groups, such as colloidal gold.

In an especially preferred embodiment, the swab member is placed on a lateral flow test strip. With this step the collected specimen is transferred directly on an immunochromatographic or enzymatic test strip. The test strip consists of one or several capillary active fleeces or membranes. The detection process will be either started directly with sample transfer or may require an elution medium to be applied for sample analysis. Preferably this elution medium is simple tap water. In the case of an immunochemical test strip, the chosen elution medium moves towards a detection zone and thereby passes the contact site within the collection device. The analyte is diluted by the elution medium and carried with it to the detection zone. In the detection zone the analyte is determined by qualitative and/or quantitative methods, e.g. in an immunological binding reaction.

The test strip can be made of one single chromatographic material, or preferably several capillary active materials made of the same or different materials and fixed on a carrier backing. These materials are in close contact with each other so as to form a transport path along which a liquid driven by capillary forces flows from the start zone, passing the contact site of the swab and the detection zone, towards a waste zone at the other end of the strip.

Furthermore this invention is disclosing a device and test kit for the performance of the described method.

In the method of invention, it is possible to make use of different immunological testing procedures to detect bacterial or viral constituents on one or several immunological binding reactions. In a preferred embodiment, a chromatography test strip contains:
- an application zone.
- a conjugate zone containing at least one labeled binding partner that is able to migrate with the elution medium. The binding partner is capable of specifically binding to an analyte and to a further specific reagent in the detection zone.
- a detection zone containing a first section for the detection of a first analyte, e.g. a test line, comprising an immobilized specific binding partner for the analyte, and optionally further sections for the detections of further analytes, and at least one control section, e.g. a control line comprising an immobilized specific binding partner of an indicator substance indicating the functionality of the test kit.

In a preferred embodiment, the specific binding partners for the analytes in the conjugate and the detection zone are monoclonal, polyclonal or recombinant antibodies or fragments of antibodies capable of binding to a pathogen. On the other hand, the specific binding partners may also be antigens capable of binding to antibodies against a pathogen or an allergen. Other types of binding partners are bioorganic macromolecules like aptamers or receptors. The conjugate zone may be located before, within or after the sample application zone, seen in the running direction of the eluent liquid. The test line(s) is(are) located after the conjugate/application zone and the control line(s) is(are) located after the test line. Together, the test line(s) and control line(s) comprise the detection zone.

Depending on the type of detection method, different binding partners are present in the different zones. In a sandwich immunoassay, it is preferred to have a labeled, non-immobilized analyte binding partner in the conjugate zone. The binding partner forms a complex with the analyte which is bound to the immobilized binding partner at the test line. In a preferred manner, the label of the conjugate binding partner is an optically detectable label. Forming a complex at the test line concentrates and immobilizes the label and the test line gets visible for the bare eye, indicating a positive test result. Particularly preferred are direct labels, and more particularly gold labels which can be best recognized by the bare eye. Additionally, an electronically photometrical read out device can be used to obtain more precise results and a semi-quantification of the analyte. Other labels may be latex, fluorophores or phosphorophores.

In order to test ocular fluids, a sample may be collected with a sample collection device from the patient's eye by a health care professional. The sample collection device should be wiped or dabbed slightly several times between in the inferior fornix of the lower eye lid. If necessary the collection device may be wet with sterile physiological saline to decrease patient's discomfort. This procedure is well known in the ophthalmology practice as it is necessary for collecting specimens for conventional laboratory analysis. Generally the sample collection device comprises a capillary active material suitable for receiving a body fluid sample. In a preferred manner the sample collection material is made out of fibers on the basis of cellulose, polyester, rayon or calcium alginate. However, the sample collection device can also be designed as a microengineered mechanical structure containing microcapillaries and/or microchannels.

Figure 4:
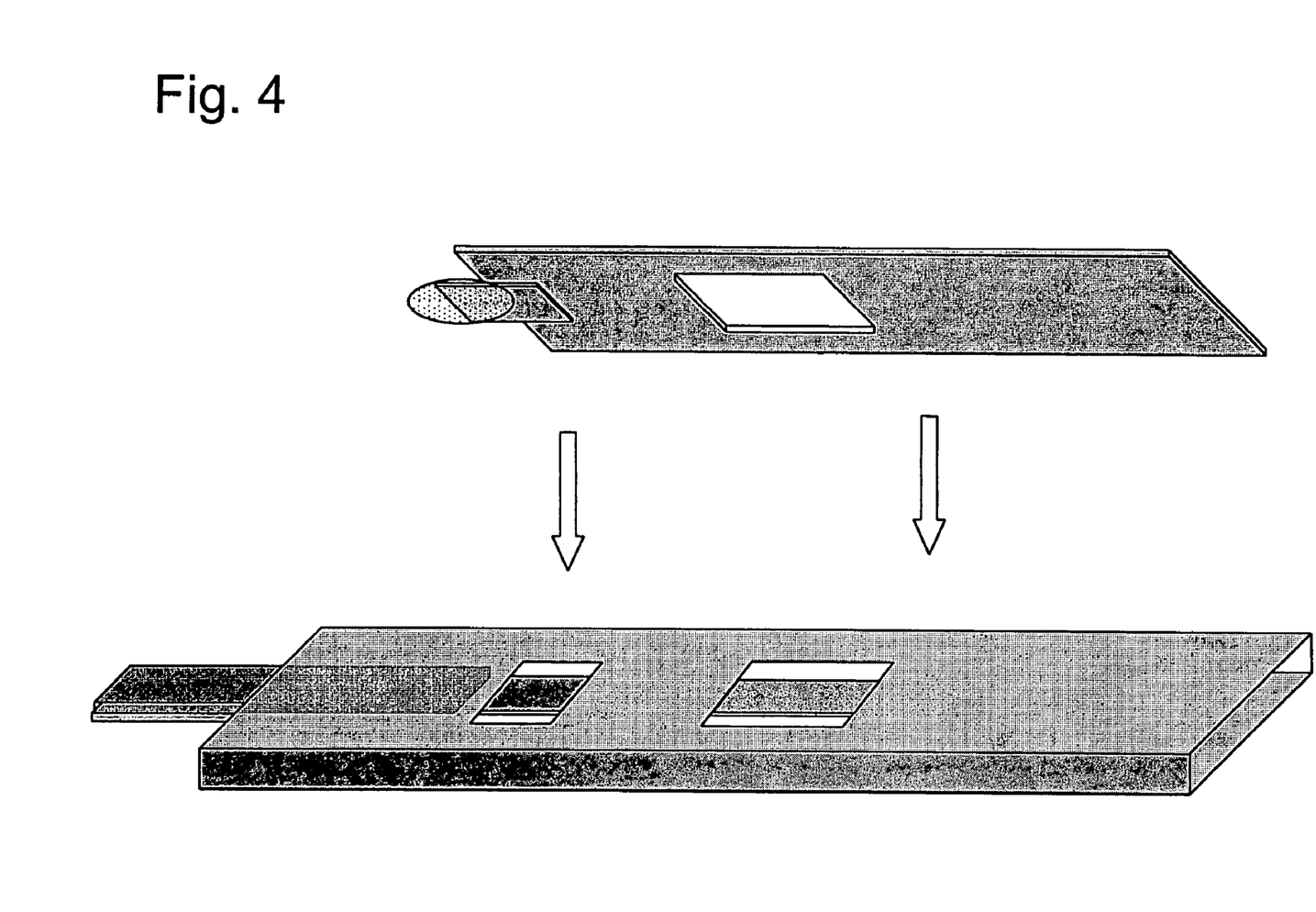
FIG. 4 shows a test kit comprising a sample analysis device according to FIGS. 1 and 2 and a swab member according to FIG. 3.

After the sample is collected, the collection device is fixed to the plastic housing containing the test strip (FIG. 4) and thereby the collection applicator is slightly pressed on the application zone of the strip. The collection device remains in this position.

In an alternative embodiment, the sample is taken by a standard swab member as currently used in the physician's office or emergency rooms. This swab member is subsequently pressed into the application zone of the chromatographic test strip by means of an additional device similar to the sample collection unit.

In another preferred embodiment, the sample is taken by a swab member and the sample collection devices is pressed for only a short time into the application zone of the chromatographic test strip. A short period of time preferably means a time up to 20 seconds, particularly between 0.1 and 10 seconds. A transfer of the sample is happening within the contact period.

In the next step, an elution medium is applied by dipping the absorbent pad into the chromatographic liquid. The absorbent pad is made of a particularly well-absorbing material which delivers the liquid for the immunochemical or enzymatic reactions. Preferred elution media are water or buffer solutions that are conventionally used in immunoassays.

Alternatively the elution medium is contained in a reservoir which may be integrated within the analysis device, e.g. as an ampoule or a blister. The reservoir may be opened by fixing the swab member or sample collection device on the detection part of the device or by additional means.

After a time period of up to 15 minutes, preferably within two to five minutes, the result can be read out in the detection zone. The result is considered positive when at least a partial area of the test line and the control line shows a color change.

EXAMPLE

Test kit for the detection of adenovirus from patient's eye swab

Figure 1:
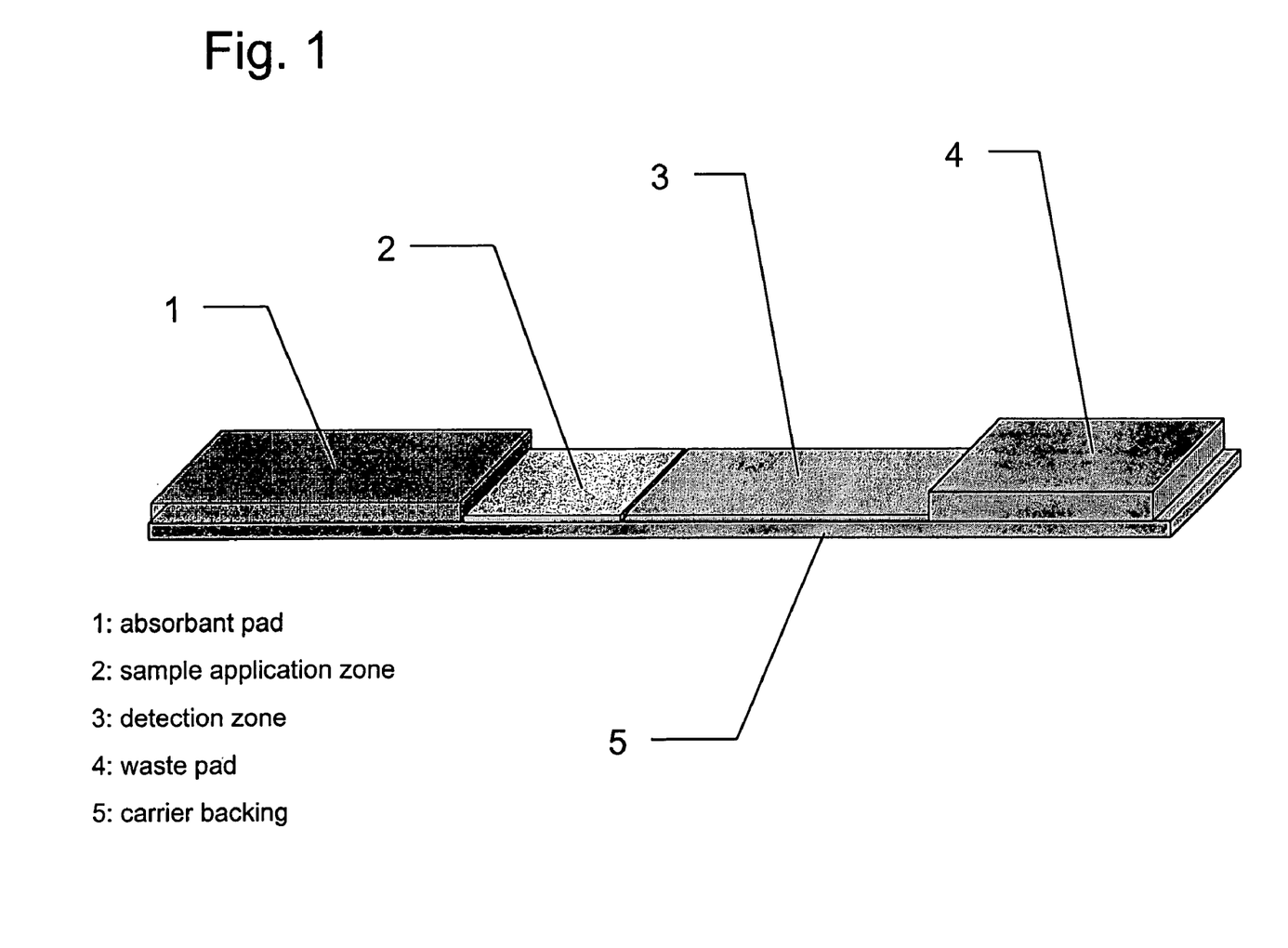
FIG. 1 shows a sample analysis device in the form of a chromatographic test strip comprising a plurality of different strip materials building an absorbent pad (1), an application zone (2), a detection zone (3) and a waste zone (4). The strip materials are arranged on an adhesive plastic backing (5). The absorbent pad (1) is providing for adding an elution medium in order to facilitate the transfer of the sample to the detection zone (3).
Figure 2:
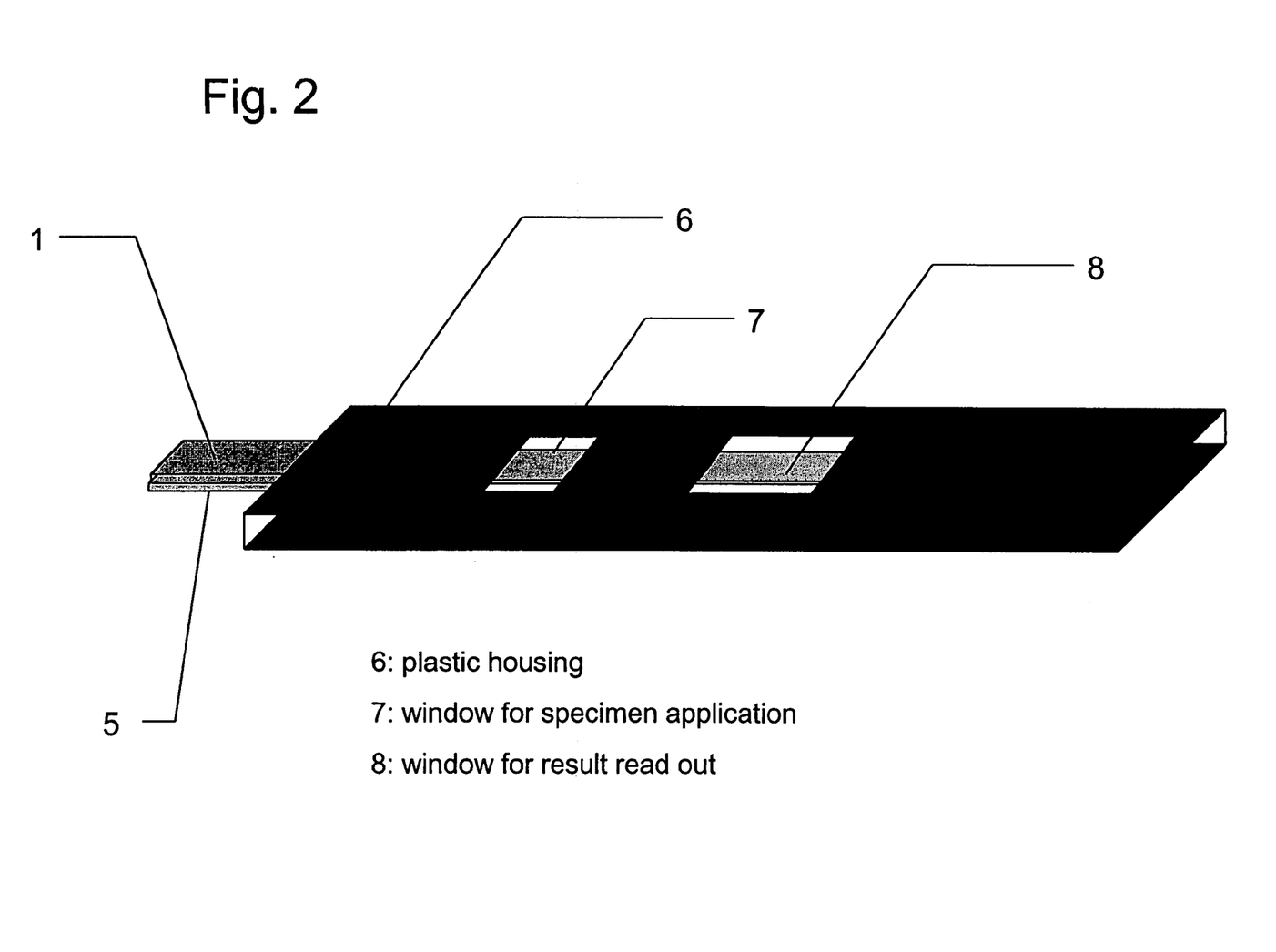

The structure of a test strip is depicted in FIG. 1.

The polyester fleece for the absorbent pad was manufactured by Binzer, Hatzfeld, Federal Republic of Germany. The fleece is a polyester fleece reinforced with 10% curalon. The thickness ranges 1 and 2 mm, the absorbance capacity is 1800 ml/m$^2$.

The application/conjugate zone consists of 80 parts polyester and 20 parts viscous staple fibers at a thickness of 0.32 mm and an absorbing capacity of 500 ml/m$^2$. The fleece is impregnated with the following solutions and then dried: 100 mmol/l HEPES Buffer, pH 7.5, 100 mol/l NaCl, conjugate of gold particles and anti-Hexon antibodies at a concentration that has an optical density of 10 at 520 nm. Hexon is a protein that is common in the capsid of human adenoviruses. The gold sol was manufactured according to standard procedures (Fres. Nature Vol. 241, p. 20-22, 1973). Conjugation with the antibody was carried out according to prior art procedure (J. Immunol. Meth. Vol. 34, p. 11-31, 1980). The sample application takes place in the application/conjugate zone.

The detection zone consists out of a nitrocellulose (NC) membrane with a nominal pore size of 8 µm and a thickness of 100 µm produced by Schleicher & Schuell, Germany. The test line contains a Hexon specific antibody (not labeled) which is specific for a different epitope than the antibody immobilized on the gold. The control contains the same antibody than the test line and binds any excess of Hexon specific gold. The control line will appear in any case even if Hexon is not present indicating that the test worked correctly.

The chromatographic materials are in communication with each other in order to create a fluid pathway.

Figure 3:
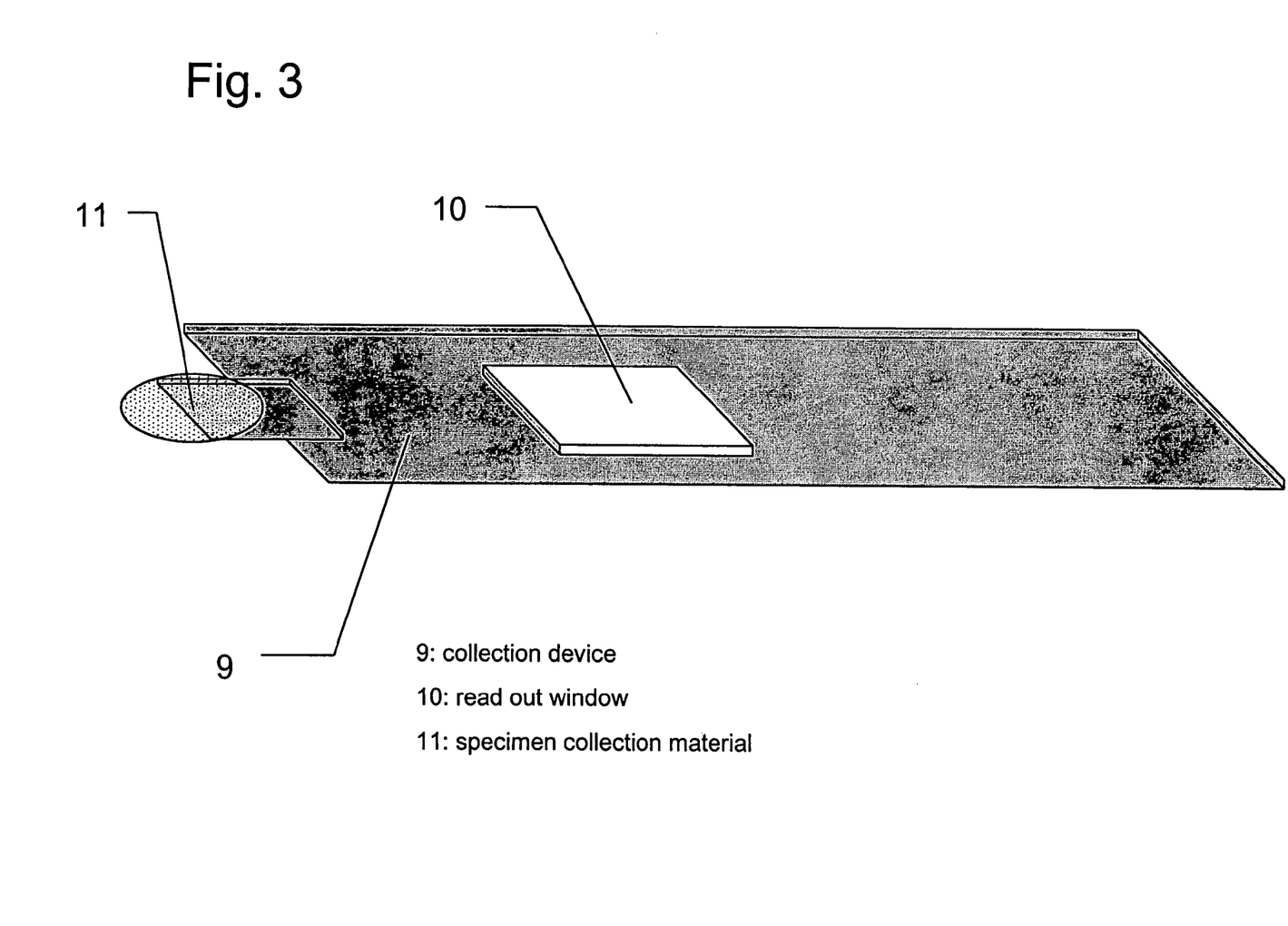
FIG. 3 shows a swab member or collection device for collecting a sample. The swab member comprises a plastic body (9) with a sample collection material (11) fixed on it and an opening (10) corresponding to a read out window when the swab member is operatively in contact with a test strip.

A sample collection device is depicted in FIG. 3. The sample collection material may consist of bibulous material such as highly purified cotton fibers which are fixed to the plastic device by ultrasonic welding. Alternative materials may be polyester, rayon, polyamide or other fibrous polymeric materials.

A test kit for the detection of Adenovirus antigen (as described in the example above) was used in the Emergency Room of an Ophthalmologic Hospital to diagnose the clinical picture of a "pink" eye. From every patient which has been tested with the test kit a second sample was taken and analysed in the laboratory.

The laboratory reference method used in this study was a combination of cell culture and immunfluorescence (IF) detection (Rodrigues et al., Ophthalmology, March 1979;86 (3):452-64) which is the current "laboratory gold standard" for determining the presence of adenovirus in human ocular fluid.

Within the testing period the following results have been achieved:

|  |  | Cell Culture/IF | |
| --- | --- | --- | --- |
|  |  | + | − |
| Adeno test kit | + | 5 | 2 |
|  | − | 0 | 21 |

These preliminary results are equivalent to a diagnostic sensitivity of 100% and a diagnostic specificity of 91%. These values are superior to diagnostic characteristics of other state of the art point-of-care devices.

The invention claimed is:

1. A method for diagnosing conjunctivitis comprising the steps:
   (a) non-invasively collecting a 0.1-100 µl eye fluid sample with a sterile swab member,
   (b) directly contacting said swab member with a sample application zone without pretreatment of said sample on a sample analysis device wherein at least a part of said eye fluid sample is released directly into said sample application zone due to said swab member contacting said sample application zone,
   (c) applying an elution medium to an absorbent pad on said sample analysis device to thereby transfer said sample to a detection zone comprising at least one immobilized binding partner, and
   (d) analyzing the sample for the presence of at least one analyte related to conjunctivitis selected from the group consisting of at least one causative agent of conjunctivitis, at least one mediator of conjunctivitis, and both at least one causative agent of conjunctivitis and at least one mediator of conjunctivitis,
   wherein said sample application zone and said detection zone are on a chromatographic test strip, and further comprising a conjugate zone between said absorbent pad and said sample application zone, wherein said conjugate zone comprises at least one labeled binding partner that is able to migrate with the elution medium.

2. The method of claim 1 wherein the sample is analyzed for the presence of a pathogen which is a causative agent of conjunctivitis or a plurality of such causative agents.

3. The method of claim 2 wherein the sample is analyzed for the presence of a pathogen selected from the group consisting of adenoviruses, herpes viruses, chlamydiae, cytomegaloviruses, amoebae and combinations thereof.

4. The method of claim 1 wherein the sample is analyzed for the presence of an allergy-associated component which is a causative agent or a mediator of conjunctivitis or a plurality of such causative agents and/or mediators.

5. The method of claim 1 wherein the sample is analyzed for the presence of a pathogen which is a causative agent of conjunctivitis or a plurality of such causative agents and at least one allergy-associated component which is a causative agent or a mediator of conjunctivitis or a plurality of such causative agents and/or mediators.

6. The method according to claim 1, wherein said eye fluid sample is 0.2-20 µl.

7. The method according to claim 1, wherein said eye fluid sample is 10-20 µl.

8. The method according to claim 1, wherein said swab member comprises a polyester fleece sample collection material.

9. The method according to claim 1, wherein said swab member directly contacts said sample application zone for less than or equal to twenty seconds.

10. The method according to claim 9, wherein the swab member directly contacts said sample application zone for between 0.1 and 10 seconds.

11. The method of claim 1, farther comprising the step of:
   (e) determining at least one result of an analysis performed in step (d) within 20 minutes of collecting the sample in step (a).

12. The method of claim 11, wherein the result is determined within 15 minutes of collecting the sample in step (a).

13. The method of claim 11, wherein the result is determined within two to five minutes of applying the elution medium in step (c).

* * * * *

UNITED STATES PATENT AND TRADEMARK OFFICE
CERTIFICATE OF CORRECTION

PATENT NO. : 7,723,124 B2
APPLICATION NO. : 11/052748
DATED : May 25, 2010
INVENTOR(S) : Aberl et al.

It is certified that error appears in the above-identified patent and that said Letters Patent is hereby corrected as shown below:

Column 8, line 49: replace "farther" with "further"

Signed and Sealed this

Seventeenth Day of August, 2010

David J. Kappos
*Director of the United States Patent and Trademark Office*